United States Patent [19]

Le et al.

[11] Patent Number: 4,895,806

[45] Date of Patent: Jan. 23, 1990

[54] DEVICE FOR LIQUID CHROMATOGRAPHY OR IMMOBILIZED ENZYME REACTION

[75] Inventors: Minh S. Le, Gateshead; James A. Sanderson, Wallsend, both of England

[73] Assignee: Millipore Ireland B.V., Roterdam, Netherlands

[21] Appl. No.: 366,312

[22] Filed: Jun. 13, 1989

Related U.S. Application Data

[63] Continuation of Ser. No. 156,290, Feb. 16, 1988, abandoned.

[30] Foreign Application Priority Data

Feb. 14, 1987 [GB] United Kingdom ............... 8703471
Apr. 27, 1987 [GB] United Kingdom ............... 8709907

[51] Int. Cl.$^4$ ............................................. C12M 1/40
[52] U.S. Cl. .................................. 435/288; 435/310; 435/311
[58] Field of Search ................. 435/288, 311, 310

[56] References Cited

U.S. PATENT DOCUMENTS

| | | | |
|---|---|---|---|
| 4,266,026 | 5/1981 | Breslau | 435/288 X |
| 4,463,473 | 1/1984 | Kleinstreuer | 435/311 X |
| 4,517,291 | 5/1985 | Seago | 435/288 X |
| 4,661,458 | 4/1987 | Berry et al. | 435/311 |

Primary Examiner—Larry Jones
Attorney, Agent, or Firm—Hamilton, Brook, Smith & Reynolds

[57] ABSTRACT

A device for separating molecular components from liquids. A multi-layer microporous membrane assembly is located within the housing (1) with edges of each membrane within the assembly lying adjacent to a barrier. Means (5,6) are provided for substantially preventing flow between the membrane edges and the barrier, so that flow is through the membranes in series. Inlet means (2) direct incoming liquid on to a first surface of the membrane assembly, and outlet means (3) gather and direct outgoing liquid from a second surface of the membrane assembly. The membrane material of the assembly has a ligand or an immobilized enzyme bound thereto for effecting chromatographic separation or an immobilized enzyme reaction.

15 Claims, 2 Drawing Sheets

DEVICE FOR LIQUID CHROMATOGRAPHY OR IMMOBILIZED ENZYME REACTION

This is a continuation of co-pending application Ser. No. 156,290 filed on Feb. 16, 1988, now abandoned.

This invention is concerned with a device for the separation of molecular components from liquids containing same. Such separations involve interactions between said components and active chemical species which are immobilised to the structure of polymeric membranes. The invention is particularly concerned with compounds for analytical or preparative purposes. The invention is also concerned with chemical reactions involving immobilised enzymes.

Separation of molecular components contained in a liquid by chromatographic techniques generally involves a two step process. First the feed is brought into contact with the separation medium whereupon the component to be separated (hereafter referred to as ligate) is preferentially bound to the active sites on the medium. The feed is then replaced by an eluent which is usually a buffer for the ligate whereupon said ligate is released to the eluent to complete the separation. A review of common ligand chromatographic techniques can be found in the work of Robert Scopes entitled "Protein Purification Principles and Practice" (published by Springer-Verlag, New York, 1982, ISBN 0-387-90726-2). In general, a separation medium consists of an active group hereafter referred to as a ligand which is chemically bonded to a solid matrix. The ligand can be any chemical species that show specific interaction with another molecular component. Known ligands include charged groups (such as diethyl amino ethyl, carboxyl methyl); synthetic dyes; alkyl and aryl compounds (such as phenyl boronate, octyl); proteins; lectins; antibodies; antigens, enzymes and so on. Ligates, that is compounds which can be separated by chromatographic techniques include a wide range of biochemicals such as proteins; enzymes; peptides; antibodies; antigens; lectins; DNA; RNA; antibiotics; etc. Traditionally the matrices used in chromatography are in the form of either beads or fibres, commonly packed into columns or less commonly in stirred vessels which provide the means for introducing the feed and for recovering the separated components.

It has been proposed to utilise microporous polymeric membranes as the solid matrix, in place of the traditional matrices, the ligand being bound to the membrane material so that the ligate is held as the feed passes through the membrane. However, no membrane device has been proposed which gives a performance equivalent to that of a good chromatographic device.

In contrast to liquid chromatography, the process of immobilised enzyme reaction can be effected by bringing the feed into contact with the reaction medium whereupon the substrate is converted into the desired product. It is to be understood that the reaction medium consists of the enzyme which is immobilised to a solid matrix. The term "substrate" refers to a component in the feed and is required to be converted by the enzyme. In general, the matrices and the columns or vessels which can be used for liquid chromatography may also be used for immobilised enzyme rections. Reference is made to Volume XLIV of "Methods in Enzymology"- ('Immobilized Enzymes' edited by K. Mosbach, Academic Press, New York, 1976). Once again, it is known to attach reaction medium to a microporous membrane, but the performance of existing devices is poor.

Accordingly, a need exists in the process industry for devices for liquid chromatography and reactions involving immobilised enzymes, which devices provide high resolution or good diffusional characteristics and high throughput rate without the use of high pressure and without any significant operational drawbacks.

According to the present invention a device for the separation of molecular components from liquids containing the same comprises a housing, a multi-layer microporous membrane assembly within the housing with edges of each membrane within the assembly lying adjacent to a barrier, means for substantially preventing flow between the membrane edges and the barrier, inlet means for directing incoming liquid on to a first surface of the membrane assembly, and outlet means for gathering and directing outgoing liquid from a second surface of the membrane assembly, the membrane material of the assembly having bound thereto a ligand or an immobilised enzyme.

In the field of liquid chromatography such a device can readily be constructed to match or even improve the performance of conventional chromatograph columns, even though the structure is simpler and more compact than that of conventional columns. Liquid chromatography devices are generally specified in terms of the number of theoretical plates hereinafter referred to as N; the height of a theoretical plate hereinafter referred to as HETP; the protein binding capacity and the dilution factor hereinafter referred to as DF. The devices of the invention can readily be manufactured such that N is at least 100; HETP is less than 0.01 cm and DF is not greater than 6. The protein binding capacity can readily be comparable with traditional columns in terms of mass of protein per unit volume of device. Prior art membrane devices do not meet any of the above requirements, and in particular they have very low protein binding capacity.

The microporous membranes used in the device have a pore size of from 0.05 to 10 microns, and they will usually have been made by the phase inversion process. A general account of membranes and their manufacture is contained in "Synthetic Polymeric Membranes" by Kesting (published by McGraw-Hill Book Company, New York, 1971).

The membrane assembly preferably comprises at least fifty membrane layers. More desirably, in excess of 100 layers are used and constructions with up to 10,000 layers are contemplated.

The membrane assembly may comprise a stack of flat membranes laid face to face, or a membrane sheet wound around a porous core to form a plurality of layers.

In the first case, preferably the barrier is formed by side wall means of the housing, and the means for substantially preventing flow between the membrane edges and the side wall means comprise first resilient sealing means between a first end wall of the housing and the periphery of the first membrane of the stack, second resilient sealing means between a second end wall of the housing and the periphery of the last membrane of the stack, and a plurality of resilient sealing washers interposed between the periphery of two adjacent membranes at intervals through the stack, the sealing means, and sealing washers each having a circumferential surface making contact with the side wall means. Sealing members will usually be present in the stack at intervals of from five to ten membranes, although intervals outside this range can be used.

Preferably the inlet means includes flow distribution means effective to distribute incoming liquid over a substantial area of the housing before the liquid makes contact with the first surface of the membrane assembly.

The devices disclosed herein may be used with any microporous membrane material capable of providing sites within its internal structure for attachment of active ligands or enzymes.

Microporous membranes have a pore size between 0.05 and 10 microns, and those with pore size between 0.1 to 10 microns are particularly useful in the device of the invention since they offer both high internal surface area and high flowrate at very modest pressure.

The membrane material used in devices for liquid chromatography should not show non-specific binding, that is indiscriminate binding of substances and should allow attachment by covalent bonding of ligands onto its structure. As far as can be determined, of all the presently commercially available microporous membranes, only membranes of regenerated cellulose satisfy both criteria simultaneously. The term "regenerated cellulose membranes" refers to membranes cast from cellulose esters such as cellulose acetate or cellulose nitrate which after the phase inversion process are converted to cellulose by hydrolysis of the nitrate or acetate groups. It should be understood that only the exposed structure of the membrane need to fulfil the criteria. For example it should be possible to coat a non-cellulose membrane with a material similar to cellulose such as dextran or poly hydroxyalkyl alkylacrylate. In effect one creates a microporous membrane composite suitable for liquid chromatography from two materials which by themselves cannot form such membrane.

In order to provide a microporous membrane suitable for covalent bonding of ligands it is desirable that the exposed surface of the membrane matrix has hydroxyl groups (OH) in abundance. The ligands may be bonded directly or indirectly via a spacer or coupling molecule by reacting with the hydroxyl groups and forming covalent bonds with the matrix. Ligands or spacer molecules which may be bonded to the matrix in the described manner will generally contain at least one group selected from halogen, epoxide, vinyl sulphone, CDI (carbonyl-di-imidazole) and CNBr.

In enxyme immobilisation non-specific binding is not an important consideration. Indeed, the non-specific binding process can be used advantageously where the membrane surface chemistry does not allow direct attachment of the enzyme by covalent bonding. A binder material can then be adsorbed into the membrane, forming a coat which permits covalent bonding of the enzyme to the coat. Since neither non-specific binding nor direct attachment to the membrane by covalent bonding are essential, any microporous membrane may be employed. U.S. Pat. No. 4,572,897 to Amotz et al, shows a preparation method for immobilised enzyme with the use of a discontinuous phase particulate inert filler material and a continuous phase hydrophilic binder material. Any known binder material may be used in the present invention. The coat of binder may be applied before or at the same time as the enzyme. In all cases the binder coat must be stabilised, that is prevented from leaching by a cross-linking reaction. The enzyme in turn is immobilised to the coating by the same cross-linking reaction. Suitable cross-linking agents must contain at least two functional groups, selected from for example halogen, epoxide, vinyl sulphone, water soluble carbodiimide and aldehyde.

In order that the invention may be better understood, specific embodiments of devices for liquid chromatography and for immobilised enzyme reaction in accordance therewith will now be described in more detail by way of example only, with reference to the accompanying drawings in which.

Figure 1:
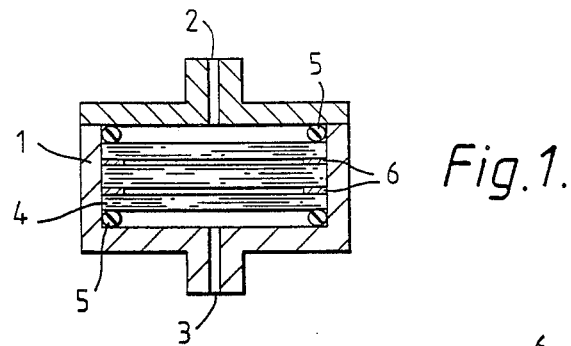
FIG. 1 shows diagrammatically a first embodiment of a device according to the present invention.

FIG. 1 shows a device embodying the invention and comprising a circular-section housing 1 having inlet 2 and outlet 3. Located within the housing 1 are a plurality of membrane discs 4 stacking one on top of another. The membrane discs are separated into groups by means of washers 6 and the whole assembly is compressed between two compression rings 5. The compression ring 5 on top also seals the top membrane against the ceiling of the housing 1 while the bottom compression ring 5 seals the bottom membrane against the floor of the housing. The outer circumference of each compression ring and each washer lies in contact with the inner surface of the cylindrical side wall of the housing. It has been found that this arrangement of compression rings and one or more washers to separate the membrane discs into groups as shown in the drawing provides a particularly efficient seal so that all the liquid flow passes through the membrane discs rather than between the wall of the housing and the outside of the discs.

The device shown illustrates three groups of membrane discs, adjacent groups being separated by a washer. While the number of discs in a group may vary there will generally be 5 to 10 discs in each group. The number of groups may obviously be more than three, and devices incorporating up to 2,000 discs have been made, while devices incorporating up to 10,000 discs are contemplated. Obviously, larger housings will be required to accommodate greater numbers of discs.

In use, feed liquid supplied to the inlet 2 flows downwardly through the stack of discs, passing through the discs in series, before exiting through outlet 3. Radial flow is prevented by the compression around the perimeter of the discs caused by the compression rings 5 and the washers 6. As the feed flows through the membrane matrix the molecular component of interest is selectively sequestered by the ligand attached to the membranes. In order to recover said component of interest a buffer solution is then flowed through the device whereupon said component is released into the buffer solution.

Where the attached ligand is an enzyme as in the case of an immobilised enzyme reaction, chemical conversion takes place as the substrate molecule comes in contact with the enzyme. The product or products of the conversion is released back into the feed stream and removed through the outlet 3.

Figure 2:
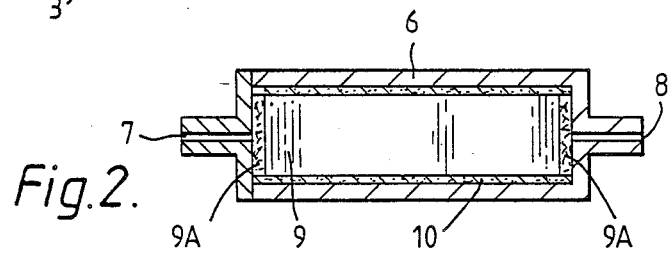
FIG. 2 shows diagrammatically a second embodiment of a device according to the present invention.

FIG. 2 shows a variation of the device shown by FIG. 1. This embodiment comprises a housing 6 having inlet 7 and outlet 8. Located within the housing 6 are a plurality of membrane discs 9 stacking one on top of another. A sealant 10 provides an effective seal between the membrane discs themselves and between the edges of the discs and the housing wall 6. Additionally, porous substrates 9A may be employed at the inlet 7 and outlet 8 in order to improve the flow distribution. Again, any required number of discs can be used.

In use, the second embodiment functions in exactly the same manner as the first embodiment already described.

Figure 3:
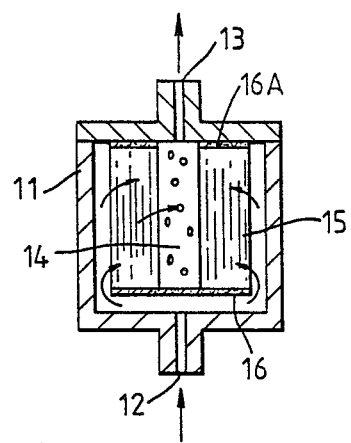
FIG. 3 shows diagrammatically a third embodiment of a device according to the present invention.
Figure 4:
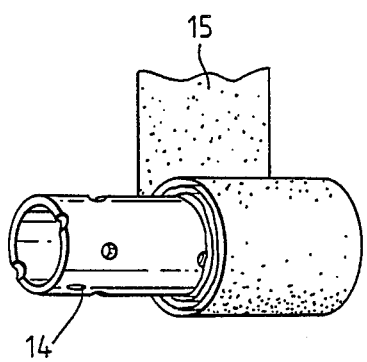
FIG. 4 is a further view of part of FIG. 3.

The third embodiment of the present invention is shown by FIG. 3 and comprises a housing 11 having inlet 12 and outlet 13. Located within the housing 11 is a membrane 15 which is wound onto a porous core 14 as further illustrated by FIG. 4 to build up any required number of layers. A barrier 16 of sealant composition seals off the lower edge of the membrane and the lower end of the porous core 14. Another barrier 16A of sealant composition seals off the upper edge of the membrane but allows fluid communication between the porous core 14 and the outlet 13.

In use, the liquid feed supplied to the inlet 12 flows radially through the layers of membrane wrap and exits through the porous core 14 then the outlet 13 as indicated by the arrows. The action of the ligand or the immobilised enzyme on the microporous membrane is as described for the first embodiment.

Figure 5:
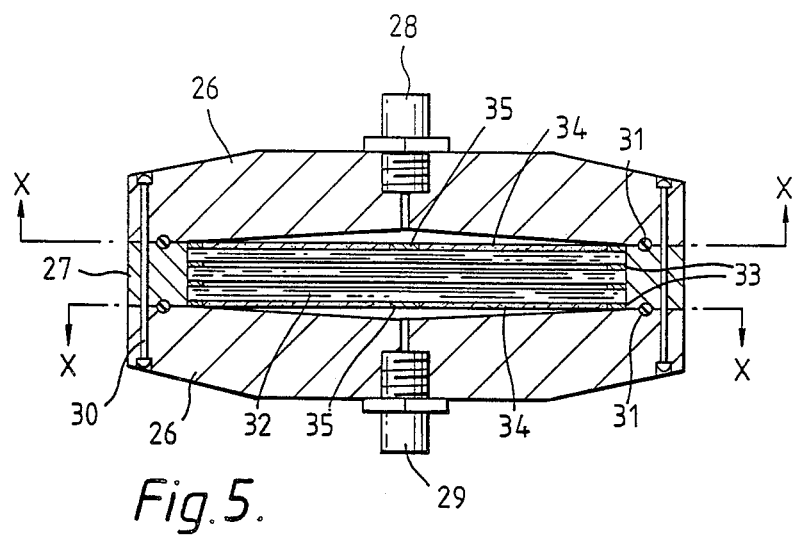
FIG. 5 shows diagrammatically a fourth embodiment of a device according to the present invention.
Figure 6:
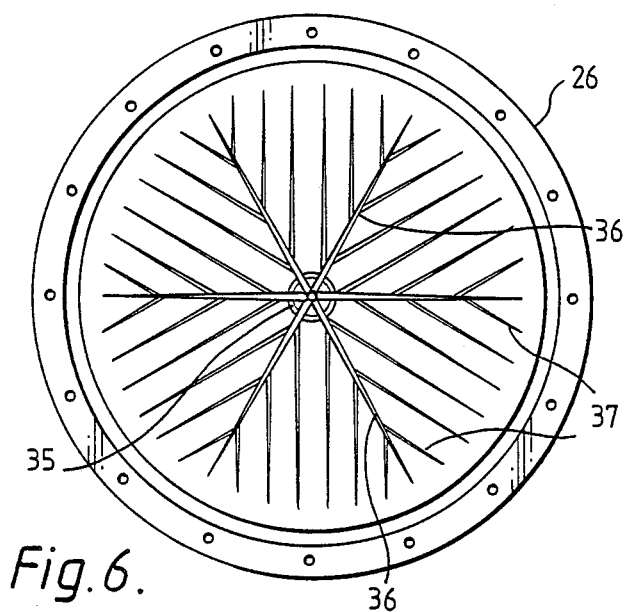
FIG. 6 is a further view of part of FIG. 5.

FIG. 5 shows a more sophisticated version of the device of FIG. 1. This embodiment comprises a housing which consists of two end plates 26 and a ring section 27, secured by a securing means 30. Two 'O' rings 31 provide a sealing means between the three housing members. Inlet means 28 and outlet means 29 are also provided. Located within the housing are a plurality of membrane discs 32 stacking one on top of another. Sealing around the circumference of the membrane discs 32, and around top and bottom porous substrates 34, is provided by a plurality of gaskets 33 which are interspersed from the top porous substrate 34 and throughout the membrane stack to the bottom porous substrate 34. Located directly underneath the inlet 28 is an anti-jetting disc 35. Similarly, there is an anti-jetting disc 35 located at the outlet 29. The purpose of the anti-jetting discs is to prevent fluid impinging at a high velocity onto the membranes and to ensure an orderly fluid exit from the device. It should be understood that the anti-jetting discs may alternatively be an integral part of the end plates 26, when manufacturing could be simplified. FIG. 9 shows a view of the endplates 26 taken from line XX. Each endplate 26 provides a network of flow channels 36 and 37 which produces a uniform distribution of the inlet fluid across the cross-sectional area of the device. The same network of channels when used in conjunction with the outlet provides a fluid collection system which will minimise any mixing of the fluid.

It has been found that in order to obtain a good flow distribution system for chromatographic columns the following conditions must be met simultaneously:

(i) the total void volume in the channels must not exceed 1% of the column volume; preferably not exceeding 0.5%;
(ii) the flow regime in all channels should preferably be constant with a Reynolds number not exceeding 1500 under normal operating conditions. Preferably the Reynolds number should be between 5–500 where the Reynolds number is defined as the hydraulic diameter of the channel times the linear velocity divided by the fluid kinematic viscosity in any consistent units;
(iii) the direct distance between any two adjacent channels, that is to say, the sum of the shortest paths from any point to the two nearest channels should not exceed one tenth of the column diameter; preferably less than one fifteenth of that diameter.

The system of channels shown in FIG. 9 is one of a number of dentritic systems which meet the above conditions. A dendritic system of channels may comprise at least 3 primary channels 35 equally spaced and radiating from the inlet point or the outlet point of the device with secondary channels 36 emanating at an angle less than 90° from said primary channels. Preferably the angle between the primary and secondary channels should be half the angle between any two adjacent primary channels. Where the diameter of the distributor exceeds 15 cm it is desirable to emply a system of tertiary channels in order to improve the distribution. Tertiary channels are channels of smaller dimensions emanating at an angle less than 90° from the secondary channels and shall not cross any channel.

Some examples of the use of the devices described will now be given. In the examples the term "membrane" refers to a regenerated cellulose membrane having a pore size of 0.45 microns or 1.2 microns unless otherwise indicated.

EXAMPLE 1

A device as shown in FIG. 2 was constructed using 2,000 membrane discs prepared by incubating a regenerated cellulose membrane in a solution containing 1% w/v Cibacron blue F3G reactive dye in water pH10 with 5% NaCl at 20° for 12 hours. The membrane contained 15 micromole dye per cc membrane. The incubated membrane was suitable for liquid chromatography. The discs have a diameter of 25 mm. The housing has an internal diameter of 35 mm. Two discs of sintered PTFE each having a pore size of 40 microns and a thickness of 1 mm and a diameter of 25 mm were used as the inlet and outlet distributors. A silicone base sealant was used as a sealing means. A 100 ml solution of 1 mg/ml human serum albumin (HSA) in 0.1 M phosphate buffer was applied to the device with a peristaltic pump at a flow rate of 5 ml/minute. The amount of protein bound was determined to be about 70 mg HSA. The bound protein was recovered by flowing a buffer containing 0.5 M KSCN through the device. The device was found to have a resolution of at least 1,500 theoretical plates as determined by a method commonly used for packed columns.

EXAMPLE 2

A device as shown in FIG. 3 was constructed with a membrane which had been prepared according to Example 1. The membrane has a width of 10 cm and was wound on a hollow and porous core with an outside diameter of 1 cm. The wound membrane has a total of 40 turns. A polyurethane thermoset resin was used as a sealing means. The membrane and the core were housed in a tube which had an internal diameter of 2 cm. The device was loaded with HSA as described in Example 1 and found to bind a total of 20 mg HSA.

EXAMPLE 3

A device as shown in FIG. 1 was constructed using 10 membrane discs of 47 mm diameter. The compression rings were rubber '0' rings with 47 mm external diameter and 2 mm in thickness. The liquid chromatography membrane discs were prepared by incubating regenerated cellulose membranes in a solution containing 1 M Chloro-diethylamino ethyl with 2M NaOH for 3 hours at 25° C. The membrane had a charge capacity of 1.01 meq/g. The device was loaded with protein by flowing 1 ml of rabbit serum which had been diluted 10 fold by 0.05 M phosphate buffer pH6.5 through the device. It was found that 150 mg of the albumin bound to the membrane. The protein was recovered by passing the same buffer with NaCl added through the device at an increasing concentration of NaCl. All the bound protein was eluted at a concentration of 0.2 M NaCl.

EXAMPLE 4

Example 3 was repeated with a liquid chromatography membrane prepared by activating regenerated cellulose membrane with a solution containing 1% 1,4 butanediol diglycidyl ether in water in the presence of 0.1 M NaOH, and incubating the membrane for 20 hours at 20° C. with a conjugate prepared by reacting Cibacron blue F3G with diaminohexane. Human plasma was used instead of rabbit serum. It was found that 5 mg HSA bound to the membrane and the protein eluted at 1 M NaCl.

EXAMPLE 5

A device as shown in FIG. 1 was constructed as described in example 3, but with an immobilised enzyme membrane. The membrane was activated with a solution containing 1 mg/ml Trypsin in 0.1 M phosphate buffer pH7 for 3 hours at 25° C. The bound enzyme had an activity that was 2% of the free state activity. A feed containing 1 mM Na-benzoyl-L-arginine ethyl ester in tris/HCl buffer pH8 was pumped through the device at 1 ml/min. The substrate was converted to Na-benzoyl-L-arginine and ethanol.

The effectiveness of devices according to the invention will be appreciated from the foregoing examples.

What is claimed:

1. A device for the separation of molecular components from liquids containing the same, comprising a housing, a multi-layer microporous membrane assembly within the housing wherein a plurality of membrane layers are disposed in face-to-face relation with edges of each membrane within the assembly lying adjacent to a barrier, means for substantially preventing flow between the membrane edges and the barrier, inlet means for directing incoming liquid on to a first surface of the membrane assembly, and outlet means for gathering and directing outgoing liquid from a second surface of the membrane assembly, wherein the flow of liquid is successively through the plurality of membrane layers, the membrane material of the assembly having bound thereto a ligand or an immobilised enzyme.

2. A device according to claim 1 in which the membrane assembly comprises at least 50 membrane layers.

3. A device according to claim 1 in which the barrier is formed by side wall means of the housing, and the means for substantially preventing flow between the membrane edges and the side wall means comprise first resilient sealing means between a first end wall of the housing and the periphery of the first membrane of the stack, second resilient sealing means between a second end wall of the housing and the periphery of the last membrane of the stack, and a plurality of resilient sealing washers interposed between the periphery of two adjacent membranes at intervals through the stack, the sealing means and sealing washers each having a circumferential surface making contact with the side wall means.

4. A device according to claim 3 in which sealing washers are present in the stack at intervals of from 5 to 10 membranes.

5. A device according to claim 3 in which the side wall means is a circular cylindrical wall, the membranes are circular discs and the sealing means and washers are each annular.

6. A device according to claim 1 in which the edges of the membranes lie adjacent to side wall means of the housing, and the means for substantially preventing flow between the membrane edges and the side wall means comprises a sealant composition bonded to the side wall means and to the peripheral regions of the membranes forming the stack.

7. A device according to claim 1 in which the inlet means includes flow distribution means effective to distribute incoming liquid over a substantial area of the housing before the liquid makes contact with the first surface of the membrane assembly.

8. A device for the separation of molecular components from liquids containing the same, comprising a housing, a multi-layer microporous membrane assembly within the housing comprising a membrane sheet wound around a porous core to form a plurality of layers with the edges of each layer lying adjacent to a barrier, means for substantially preventing flow between the membrane edges and the barrier, inlet means for directing incoming liquid on to a first surface of the membrane assembly, and outlet means for gathering and directing outgoing liquid from a second surface of the membrane assembly, the membrane material of the assembly having bound thereto a ligand or an immobilised enzyme.

9. A device according to claim 8 in which the wound edges of the membrane sheet abut against a barrier formed by sealant composition bonded to the edge regions of the membrane sheet, the composition also forming the means for substantially preventing flow between the membrane edges and the barrier.

10. A device for the separation of molecular components from liquids containing the same, comprising a housing, a multi-layer microporous membrane assembly within the housing with edges of each membrane within the assembly lying adjacent to a barrier, means for substantially preventing flow between the membrane edges and the barrier, inlet means for directing incoming liquid on to a first surface of the membrane assembly including a flow distribution means effective to distribute incoming liquid over a substantial area of the housing before the liquid makes contact with the first surface of the membrane assembly comprising a porous disc overlying the first surface of the membrane assembly, said disc having a solid, non-porous section immediately aligned with an inlet opening, and a distributor arrangement for distributing incoming liquid over the surface of the porous disc, and outlet means for gathering and directing outgoing liquid from a second surface of the membrane assembly, the membrane material of the assembly having bound thereto a ligand or an immobilised enzyme.

11. A device according to claim 10 in which the inlet opening is formed in a cap forming an end wall of the housing, an inner surface of the cap lies in contact with the porous disc, and the distributor arrangement comprises a series of channels formed in the inner surface of the cap.

12. A device according to claim 11 in which the total void volume in the channels does not exceed 1% of the volume of the membrane assembly.

13.. A device according to claim 11 in which the flow regime throughout the channel system is substantially constant with a Reynolds number not exceeding 1500 under normal operating conditions.

14. A device according to claim 11 in which the cap is circular, the inlet is at the centre of the cap, and the channels form a dendritic arrangement radiating outwardly from the centre of the cap.

15. A device according to claim 14 in which the sum of the shortest paths from any point on the inner surface of the cap to the two nearest channels does not exceed one tenth the diameter of the membrane assembly.

* * * * *